(12) United States Patent
Dutt et al.

(10) Patent No.: US 9,610,247 B2
(45) Date of Patent: Apr. 4, 2017

(54) USE OF A THIAZOLO PYRIMIDINONE FOR THE TREATMENT OF INFLAMMATORY BOWEL DISEASE

(71) Applicant: TORRENT PHARMACEUTICALS LIMITED, Ahmedabad (IN)

(72) Inventors: Chaitanya Dutt, Gandhinagar (IN); Vijay Chauthaiwale, Gandhinagar (IN); Ram Gupta, Gandhinagar (IN); Shitalkumar Zambad, Gandhinagar (IN); Shailesh Deshpande, Gandhinagar (IN); Jignesh Kotecha, Gandhinagar (IN); Ramesh Gupta, Gandhinagar (IN); Sanjay Srivastava, Gandhinagar (IN); Laxmikant Chhipa, Village Bhat (IN); Jaya Abraham, Gandhinagar (IN)

(73) Assignee: Torrent Pharmaceuticals Limited, Ahmedabad (IN)

( * ) Notice: Subject to any disclaimer, the term of this patent is extended or adjusted under 35 U.S.C. 154(b) by 0 days.

(21) Appl. No.: 14/890,131

(22) PCT Filed: May 12, 2014

(86) PCT No.: PCT/IB2014/000707
§ 371 (c)(1),
(2) Date: Nov. 9, 2015

(87) PCT Pub. No.: WO2014/184631
PCT Pub. Date: Nov. 20, 2014

(65) Prior Publication Data
US 2016/0120801 A1    May 5, 2016

(30) Foreign Application Priority Data

May 14, 2013 (IN) .......................... 1718/MUM/2013
Jul. 9, 2013 (IN) .......................... 2309/MUM/2013

(51) Int. Cl.
*A61K 31/519* (2006.01)
*A61K 9/00* (2006.01)
*A61K 9/20* (2006.01)
*A61K 9/28* (2006.01)

(52) U.S. Cl.
CPC .......... *A61K 9/0053* (2013.01); *A61K 9/2009* (2013.01); *A61K 9/2013* (2013.01); *A61K 9/2018* (2013.01); *A61K 9/2054* (2013.01); *A61K 9/2059* (2013.01); *A61K 9/2846* (2013.01); *A61K 31/519* (2013.01)

(58) Field of Classification Search
None
See application file for complete search history.

(56) References Cited

U.S. PATENT DOCUMENTS

2011/0130414 A1    6/2011   Srivastava et al.

FOREIGN PATENT DOCUMENTS

WO    2009/002533 A1    12/2008
WO    2011/045811 A1    4/2011

OTHER PUBLICATIONS

P. Jamadarkhana et al., "Treatment with a Novel Hypoxia-Inducible Factor Hydroxylase Inhibitor (TRC160334) Ameliorates Ischemic Acute Kidney Injury", American Journal of Nephrology, 2012, vol. 36, pp. 208-218.
A. Robinson et al., "Mucosal Protection by Hypoxia-Inducible Factor Prolyl Hydroxylase Inhibition", Gastroenterology, 2008, vol. 134, pp. 145-155.
J. Karhausen et al., "Epithelial hypoxia-inducible factor-1 is protective in murine experimental colitis", The Journal of Clinical Investigation, 2004, vol. 114, No. 8, pp. 1098-1106.
R. Gupta et al., "Theraupetic treatment with a novel hypoxia-inducible factor hydroxylase inhibitor (TRCI60334) ameliorates murine colitis", Clinical and Experimental Gastroenterology, 2014, vol. 7, pp. 13-23.
International Search Report corresponding to Application No. PCT/IB2014/000707, mailed on Jul. 24, 2014.

*Primary Examiner* — Samantha Shterengarts
(74) *Attorney, Agent, or Firm* — Daniel R. Evans; Melissa M. Hayworth (57) ABSTRACT

Present invention relates to a low dose pharmaceutical composition, preferably oral composition comprising therapeutically effective amount of [(2-hydroxy-4-oxo-6,7,8,9-tetrahydro-4H,5H-10-thia-1,4a-diaza-benzo[a]azulene-3-carbonyl)-amino]-acetic acid (compound A) in the range of 2.5 mg to 60 mg. Present invention also relates to a method of treating inflammatory bowel disease in a mammal by administrating said low dose pharmaceutical composition. Further, present invention relates to a use of the compound A for the preparation of low dose pharmaceutical composition for the treatment of inflammatory bowel disease in a mammal.

12 Claims, 8 Drawing Sheets

USE OF A THIAZOLO PYRIMIDINONE FOR THE TREATMENT OF INFLAMMATORY BOWEL DISEASE

RELATED APPLICATIONS

The present application is a 371 National Stage of PCT/IB2014/000707 filed on May 12, 2014, which claims the benefit of Indian Provisional Patent Application No. 1718/MUM/2013 filed on May 14, 2013 and Indian Provisional Patent Application No. 2309/MUM/2013 filed on Jul. 9, 2013.

FIELD OF THE INVENTION

Present invention relates to a low dose pharmaceutical composition, preferably oral composition comprising therapeutically effective amount of [(2-hydroxy-4-oxo-6,7,8,9-tetrahydro-4H,5H-10-thia-1,4a-diaza-benzo[a]azulene-3-carbonyl)-amino]-acetic acid (compound A) in the range of 2.5 mg to 60 mg. Present invention also relates to a method of treating inflammatory bowel disease in a mammal by administrating said low dose pharmaceutical composition. Further, present invention relates to a use of the compound A for the preparation of low dose pharmaceutical composition for the treatment of inflammatory bowel disease in a mammal.

BACKGROUND OF THE INVENTION

Inflammatory bowel disease (IBD) is the name given to a group of diseases causing chronic inflammation of the gastrointestinal tract. It is an idiopathic disease caused by a dysregulated immune response to host intestinal microflora. The course of IBD varies widely, with intermittent periods of remission followed by periods of acute illness. The 2 major types of IBD are ulcerative colitis and Crohn's disease.

Ulcerative colitis affects the colon and rectum and typically involves only the innermost lining or mucosa, manifesting as continuous areas of inflammation and ulceration, with no segments of normal tissue. The disease involving only the most distal part of the colon and the rectum, termed as ulcerative proctitis; disease from the descending colon down is referred to as limited or distal colitis; whereas disease involving the entire colon is called pancolitis (Kathleen Head et al; *Altern Med Rev.* 2003; 8(3):247-83).

Crohn's disease is transmural (affecting all layers of the intestine) inflammation that can affect any portion of the digestive tract from mouth to anus, but is predominantly seen in the terminal ileum and/or colon. Intestinal inflammation and ulceration in Crohn's disease is asymmetrical and occurs in "patches," with areas of healthy tissue interspersed, and extends deeply into the intestinal wall, forming granulomatous lesions. Several categories of Crohn's disease have been described, defined by the portion of the digestive tract involved and the presenting symptomatology (Kathleen Head et al; *Altern Med Rev.* 2004; 9(4):360-401). The symptoms are often more variable than ulcerative colitis depending on which part of the bowel is involved.

Clinical symptoms of IBD include abdominal cramps and pain, bloody diarrhea, severe urgency to have a bowel movement, sensation of incomplete evacuation, fever, loss of appetite, weight loss and anemia. Available therapeutic strategies for management of IBD include 5-aminosalicylate (mesalamine), corticosteroids, immunomodulators, antibiotics and anti-tumor necrosis factor (TNF) agents. Most commonly used medication for IBD is mesalamine, which is available in the dose strengths range 250 mg to 2 g, which are recommended for dose of at least 1 g per day or even higher by oral route of administration. Though mentioned therapeutic strategies are found useful, non-responsiveness of patients to 5-aminosalicylate, side-effects associated with high-level and prolonged corticosteroid usage and non-response/loss of response, high cost and increased risk of infection and malignancy with the use of biologic agents, especially when combined with immunomodulators are limiting (Cummins et al; *Lab Invest.* 2013; 93: 378-383). This indicates at existence of gap in the available therapeutics and re-inforces need for the development of newer therapeutic approaches for the treatment of IBD. Also, as mentioned, IBD is a chronic disease, the medication is required for longer duration of time, for example, mesalamine is recommended generally for 6 to 8 weeks for the total daily dose of 4 g by oral route. Therefore, high dose medication for longer duration may reduce patient compliance.

Although exact etiology for IBD is not yet established but it has been found by researchers that during IBD, increased tissue metabolism and vasculitis renders the chronically inflamed mucosa and particularly the epithelium hypoxic, giving rise to the activation of the hypoxia-responsive transcription factor hypoxia-inducible factor (HIF).

The protective role of HIF-1 in murine colitis was first investigated by Karhausen et al (*J Clin Invest.* 2004; 114: 1098-1106). Conditional deletion of HIF-1α in colonic epithelium increased the severity of colitis and barrier dysfunction in both the oxazolone- and trinitrobenzene sulfonic acid (TNBS)-induced model of acute colitis. HIF activation is also known for up-regulation of set of target genes linked with maintenance of intestinal barrier function such as HSP 70 and anti-inflammatory cytokines interleukin (IL)-10 (Braat et al; *Clinical Gastroenterology and Hepatology* 2006; 4:754-759)

Intestinal epithelial HSP70 plays an important role in protecting mucosal integrity and function by stabilizing the tight junctions between intestinal epithelial cells. Such intestinal epithelial protection is associated with restricted bacterial translocation and a reduction in inflammation (Liedel J L et al; *Pediatr Res.* 2011; 69:395-400). Also IL-10 expression is directly linked with inflammatory disorders. It was shown that IL-10-deficient mice develop a chronic bowel disease resembling Crohn's disease in human beings and intragastric administration of recombinant *lactococcus lactis* strain secreting murine IL-10, prevented onset of colitis in IL-10 knockout mice, and caused a 50% reduction of the inflammation in dextran sulfate sodium-induced chronic colitis. (Braat et al; *Clinical Gastroenterology and Hepatology* 2006; 4:754-759)

WO2009002533 discloses method for treating IBD by administering an agent that inhibits HIF hydroxylase activity. It discloses pyridine-2-carboxamide, quinoline-2-carboxamide and isoquinoline-3-carboxamide as HIF hydroxylase inhibitors for treatment of IBD. It discloses that compound was administered daily as intraperitoneal dose in TNBS induced animal model of colitis at the dose of 20 mg/kg and 40 mg/kg, and higher dose was found more effective.

Above data shows that disclosed HIF hydroxylase inhibitors may have potential in treatment of IBD in animals. However there is no conclusive evidence available yet that HIF hydroxylase inhibitor can be effective for the treatment of IBD, particularly by oral administration and there is no HIF hydroxylase inhibitor drug yet available in the market which could be used for treatment of IBD effectively.

WO2011045811 discloses oxazolo and thiazolo derivatives as HIF hydroxylase inhibitors for treatment of anemia, ischemia or tissue damage caused by ischemic disorders. It discloses that compound 10 was effective for chronic kidney disorder (CKD) at higher doses such as at the dose of 20 mg/kg bid (approx 450 mg/day equivalent human dose), when administered through intraperitoneal route to diseased animals.

Jamadarkhana et al discloses in *Am J. of nephrology* (2012, 36: 208-218) that compound [(2-hydroxy-4-oxo-6,7,8,9-tetrahydro-4H,5H-10-thia-1,4a-diaza-benzo[a]azulene-3-carbonyl)-amino]-acetic acid, a novel HIF hydroxylase inhibitor, when administered intraperitoneally it was found effective in prevention and for treatment of ischemic acute kidney injury (AKI).

Both Jamadarkhana et al and WO2011045811 teach to use HIF hydroxylase inhibitor, [(2-hydroxy-4-oxo-6,7,8,9-tetrahydro-4H,5H-10-thia-1,4a-diaza-benzo[a]azulene-3-carbonyl)-amino]-acetic acid, for the treatment of anemia, ischemia or tissue damage caused by ischemic disorder such as CKD or AKI, specifically by parenteral route.

Present invention provides a low dose pharmaceutical composition for non-parenteral administration, preferably for oral administration, comprising HIF hydroxylase inhibitor, [(2-hydroxy-4-oxo-6,7,8,9-tetrahydro-4H,5H-10-thia-1,4a-diaza-benzo[a]azulene-3-carbonyl)-amino]-acetic acid (hereinafter mentioned as compound A) which is useful in the dosage range of 2.5 mg to 60 mg per day for treating inflammatory bowel disease (herein after referred as IBD). Present invention also provides a method of treating inflammatory bowel disease in a mammal by administering low dose pharmaceutical compositions comprising therapeutically effective amount of compound A, which is effective in low dosage range of 2.5 mg to 60 mg per day.

SUMMARY OF THE INVENTION

One aspect of the present invention is to provide a low dose pharmaceutical composition comprising compound A and at least one pharmaceutically acceptable carrier selected from diluent, binder, disintegrant, pH adjusting agent and lubricant, wherein said composition is effective in the dosage range of 2.5 mg to 60 mg per day for the treatment of IBD in a mammal.

Another aspect of the present invention is to provide a low dose pharmaceutical composition for oral administration comprising compound A and at least one pharmaceutically acceptable carrier selected from diluent, binder, disintegrant, pH adjusting agent and lubricant, wherein said composition is effective in the dosage range of 2.5 mg to 60 mg per day for the treatment of IBD in a mammal.

Another aspect of the present invention is to provide a low dose pharmaceutical composition comprising compound A in an amount of 2.5 mg to 60 mg and at least one pharmaceutically acceptable carrier selected from diluent, binder, disintegrant, pH adjusting agent and lubricant, wherein the said composition is effective in treating IBD in a mammal.

Another aspect of the present invention is to provide a low dose pharmaceutical composition for oral administration comprising compound A in an amount of 2.5 mg to 60 mg and at least one pharmaceutically acceptable carrier selected from diluent, binder, disintegrant, pH adjusting agent and lubricant, wherein the said composition is effective in treating IBD in a mammal.

Another aspect of the present invention is to provide a low dose pharmaceutical composition comprising compound A and at least one pharmaceutically acceptable carrier selected from diluent, binder, disintegrant, pH adjusting agent and lubricant for the treatment of IBD in a mammal, wherein the said composition provides at least 50% local exposure of the total amount of said compound administered.

Another aspect of the present invention is to provide a method of treating IBD in a mammal, by administering a low dose pharmaceutical composition comprising therapeutically effective amount of compound A.

Another aspect of the present invention is to provide use of compound A for preparation of the low dose pharmaceutical composition for the treatment of IBD in a mammal.

BRIEF DESCRIPTION OF THE DRAWINGS

FIG. 1: Mean DAI score (FIG. 1*a*), mean macroscopy score (FIG. 1*b*) mean percent change in body weight (FIG. 1*c*) and survival rate (FIG. 1*d*) of animal model of colitis (TNBS induced colitis in male BALB/c mice) on per-oral administration of pharmaceutical composition comprising compound A or placebo (Composition without compound A).

FIG. 2: Mean DAI score (FIG. 2*a*), mean percent change in body weight (FIG. 2*b*) and mean colitis score (FIG. 2*c*) of animal model of colitis (DSS induced colitis in female BALB/c mice) or healthy animals and HSP70 protein expression in colon tissue (FIG. 2*d*) of animal model of colitis (DSS induced colitis in female BALB/c mice) on per-oral administration of pharmaceutical composition comprising compound A or placebo (Composition without compound A).

FIG. 6: Mean percent improvement in DAI scores (FIG. 6*a*) and macroscopy score (FIG. 6*b*) of animal model of colitis (TNBS induced colitis in male BALB/c mice) on intraperitoneal and per-oral administration of pharmaceutical composition comprising compound A.

DETAILED DESCRIPTION OF THE INVENTION

The following paragraphs detail various embodiments of the invention. For the avoidance of doubt, it is specifically intended that any particular feature(s) described individually in any one of these paragraphs (or part thereof) may be combined with one or more other features described in one or more of the remaining paragraphs (or part thereof). In other words, it is explicitly intended that the features described below individually in each paragraph (or part thereof) represent important aspects of the invention that may be taken in isolation and also combined with other important aspects of the invention described elsewhere within this specification as a whole, and including the examples and figures. The skilled person will appreciate that the invention extends to such combinations of features and that these have not been recited in detail here in the interests of brevity.

The term "[(2-hydroxy-4-oxo-6,7,8,9-tetrahydro-4H,5H-10-thia-1,4a-diaza-benzo[a]azulene-3-carbonyl)-amino]-acetic acid" or "compound A" as used herein is defined to mean [(2-hydroxy-4-oxo-6,7,8,9-tetrahydro-4H,5H-10-thia-1,4a-diaza-benzo[a]azulene-3-carbonyl)-amino]-acetic acid as its base or pharmaceutically acceptable salts thereof or polymorph thereof or ester thereof. Any of these said forms can be crystalline or amorphous.

The term "Inflammatory bowel disease or IBD" as used herein is the condition which results because of inflammation of epithelium, particularly gastrointestinal epithelium. It includes conditions like ulcerative colitis, Crohn's disease, collagenous colitis, lymphocytic colitis, ischemic colitis, diversion colitis, Behcet's syndrome, and indeterminate colitis.

The term "effective amount", "therapeutically effective amount" or effective dose" as used herein meaning the amount or dose of the compound A, that is sufficient to initiate therapeutic response in a mammal including human being.

The term "mammal" means a human being or an animal including monkey, primates, dogs, cats, horses or cows etc, preferably human being.

The term "dosage range" or "range" as described herein means the therapeutically effective range of the compound A, which is suitable for administration to a mammal.

The term "low dose" as described herein means the total daily dose for a mammal, preferably human being, which is less than 100 mg per day, preferably less than 60 mg per day, more preferably less than 50 mg per day. Dose conversion for different types of mammals, including human being, can be done as per FDA guidelines available on www.fda.gov. For human being, 70 kg has been considered as average weight.

The term "substantially insoluble" as used herein means at least 75% of the composition is not soluble at pH below 5. Preferably at least 80% of the composition is not soluble at pH below 5. More preferably at least 90% of the composition is not soluble at pH below 5.

The term "systemic exposure" as used herein means availability of the compound A including its active metabolites, if any, in the systemic circulation of a mammal.

The term "local exposure" as used herein means the availability of the compound A including its active metabolites, if any, at the affected site or diseased area or in its vicinity.

The term "upper GI tract" means the part of GI tract comprising esophagus, stomach and duodenum. The term "lower GI tract" means remaining part of GI tract.

The use of the terms "a" and "an" and "the" and similar references in the context of describing the invention (especially in the context of the following claims) are to be construed to cover both the singular and the plural, unless otherwise indicated herein or clearly contradicted by context.

Present invention provides that a low dose pharmaceutical composition of compound A is effective in a dosage range of 2.5 mg to 60 mg per day, for the treatment of IBD. Present invention also provides a method of treating IBD in a mammal by administering a low dose pharmaceutical composition comprising therapeutically effective amount of compound A. Compound A, which is a HIF hydroxylase inhibitor disclosed in WO201145811 for the treatment of anemia, ischemia or tissue damage caused by ischemic disorders when administered parenterally. Patent application discloses that compound 10 was found effective for chronic kidney disorder (CKD), at the dose of 20 mg/kg bid (approx 450 mg/day human dose), when administered through intraperitoneal route to diseased animals.

Inventors of present invention have found that the low dosage range of 2.5 mg/day to 60 mg/day as an optimal dosage range which achieve desired therapeutic effect, when given through non-parenteral route, preferably through oral route, for the treatment of IBD.

IBD which can be treated by administering therapeutically effective amount of compound A according to present invention includes conditions like ulcerative colitis, Crohn's disease, collagenous colitis, lymphocytic colitis, ischemic colitis, diversion colitis, Behcet's syndrome, and indeterminate colitis. Any other disease which includes inflammation of epithelium is also within the scope of present invention.

None of the prior art tried per-oral administration and mainly discloses parenteral route as preferred route of administration for HIF hydroxylase inhibitors for treatment of IBD. It is general art known to person having ordinary skilled that effective amount of any compound would mainly be dependent on the circulating concentration/plasma levels of the active moiety. Inventors of present invention have found dose 2.5 mg to 60 mg of compound A as effective dose for the treatment of IBD, when administered orally. Surprisingly, when pharmaceutical composition comprising compound A was given orally as well as intra peritoneal (IP), it was found that oral dose was more efficacious and provided more therapeutic benefit than intra peritoneal dose, with very less systemic exposure (circulating concentration/plasma levels) and high target tissue exposure as compared to IP for treatment of IBD. Hence present invention provides better therapeutic efficacy with improved safety margin.

Thus, one embodiment of the present invention provides a low dose pharmaceutical composition comprising compound A and at least one pharmaceutically acceptable carrier selected from diluent, binder, disintegrant, pH adjusting agent and lubricant, wherein said composition is effective in the dosage range of 2.5 mg to 60 mg per day for the treatment of IBD in a mammal.

Another embodiment of the present invention provides a low dose pharmaceutical composition comprising compound A and at least one pharmaceutically acceptable carrier selected from diluent, binder, disintegrant, pH adjusting agent and lubricant, wherein said composition is effective for the treatment of IBD in a mammal when administered in a dosage range of 2.5 mg to 60 mg per day.

Another embodiment of the present invention provides a low dose pharmaceutical composition comprising compound A in an amount of 2.5 mg to 60 mg and at least one pharmaceutically acceptable carrier selected from diluent, binder, disintegrant, pH adjusting agent and lubricant, wherein the said composition is effective in treating inflammatory bowel disease in a mammal.

Another embodiment of the present invention provides a method of treating IBD in a mammal by administering a low dose pharmaceutical composition comprising therapeutically effective amount of compound A.

A preferred embodiment of present invention provides a method of treating IBD in a mammal by administering a low dose pharmaceutical composition comprising therapeutically effective amount of compound A, wherein said composition is effective in the dosage range of 2.5 mg to 60 mg per day.

Another preferred embodiment of present invention provides a method of treating IBD in a mammal by administering a low dose pharmaceutical composition comprising compound A in a range of 2.5 mg to 60 mg. Said low dose pharmaceutical composition further comprises at least one pharmaceutically acceptable carrier selected from diluent, binder, disintegrant, pH adjusting agent and lubricant.

Another embodiment of the present invention provides use of compound A for preparation of a low dose pharmaceutical composition for the treatment of IBD in a mammal.

A preferred embodiment of present invention provides use of compound A for preparation of a low dose pharmaceutical composition for the treatment of IBD in a mammal wherein said composition is effective in the dosage range of 2.5 mg to 60 mg per day.

Another preferred embodiment of present invention provides use of compound A in a range of 2.5 mg to 60 mg for preparation of a low dose pharmaceutical composition for the treatment of IBD in a mammal. Said low dose pharmaceutical composition further comprises at least one pharmaceutically acceptable carrier selected from diluent, binder, disintegrant, pH adjusting agent and lubricant.

Preferably, present invention provides a low dose pharmaceutical composition for non-parenteral administration, such as oral administration of compound A.

Therefore, another embodiment of the present invention provides a low dose pharmaceutical composition for oral administration comprising compound A and at least one pharmaceutically acceptable carrier selected from diluent, binder, disintegrant, pH adjusting agent and lubricant, wherein said composition is effective in the dosage range of 2.5 mg to 60 mg per day for the treatment of IBD in a mammal.

A preferred embodiment of the present invention provides a low dose pharmaceutical composition for oral administration comprising compound A in an amount of 2.5 mg to 60 mg and at least one pharmaceutically acceptable carrier selected from diluent, binder, disintegrant, pH adjusting agent and lubricant, wherein the said composition is effective in treating inflammatory bowel disease in a mammal.

Effective dose of compound A for the treatment of IBD according to present invention ranges from 2.5 mg to 60 mg per day or its equivalent dose when present as salt or ester. Preferably, dose of the compound A is 4.5 mg to 50 mg, most preferably dose of compound A is 4.5 mg to 40 mg. Effective dose as defend herein also include the obvious modification of dosage range on either side, which does not render additional significant therapeutic benefit and/or reduce the adverse effects over specified dosage range.

It has been observed that above mentioned dosage range provide optimally efficacious dosage range wherein maximally effective concentration at desired site is achieved with minimal systemic exposure and thus provide therapeutic benefits in treatment of IBD with improved safety margin. Therefore, present invention provides a low dose pharmaceutical composition where least systemic exposure and more local exposure of compound A is provided upon administration.

Thus, another embodiment of the present invention provides a low dose pharmaceutical composition comprising compound A and at least one pharmaceutically acceptable carrier selected from diluent, binder, disintegrant, pH adjusting agent and lubricant for the treatment of IBD in a mammal, wherein the said composition provides at least 50% local exposure of the total amount of said compound administered.

Another embodiment of the present invention provides a method of treating IBD in a mammal by administering a low dose pharmaceutical composition comprising therapeutically effective amount of compound A wherein the said composition provides at least 50% local exposure of the total amount of said compound administered. Said low dose pharmaceutical composition further comprises at least one pharmaceutically acceptable carrier selected from diluent, binder, disintegrant, pH adjusting agent and lubricant.

Another embodiment of the present invention provides use of compound A for preparation of a low dose pharmaceutical composition for the treatment of IBD in a mammal, wherein the said composition provides at least 50% local exposure of the total amount of said compound administered. Said low dose pharmaceutical composition further comprises at least one pharmaceutically acceptable carrier selected from diluent, binder, disintegrant, pH adjusting agent and lubricant.

The pharmaceutical composition according to present invention provides at least 50% local exposure of the amount of compound A administered. Preferably, composition provides at least 60% local exposure of the amount of compound A administered. Most preferably, composition provides at least 70% local exposure of the amount of compound administered.

Preferably, low dose pharmaceutical composition according to present invention is non-parenteral composition; most preferably low dose pharmaceutical composition is oral composition.

One embodiment of the present invention provides a low dose pharmaceutical composition for immediate release comprising compound A and at least one pharmaceutically acceptable carrier selected from diluent, binder, disintegrant, pH adjusting agent and lubricant, for the treatment of IBD in a mammal.

Preferably, present invention provides a low dose non-parenteral composition, particularly oral composition for immediate release of compound A for the treatment of IBD in a mammal comprising compound A and at least one pharmaceutically acceptable carrier selected from diluent, binder, disintegrant, pH adjusting agent and lubricant, wherein compound A is effective in the dosage range of 2.5 mg to 60 mg.

It was noticed that the composition according to present invention shows synergistic effect when pharmaceutically acceptable carrier selected from diluent, binder, disintegrant, pH adjusting agent and lubricant are used in formulating compound A.

Another embodiment of the present invention provides a low dose pharmaceutical composition comprising compound A in an amount of 2.5 mg to 60 mg and at least one pharmaceutically acceptable carrier selected from diluent, binder, disintegrant, pH adjusting agent and lubricant wherein diluent, when used, is present in the amount of 10-98% w/w of the total composition; binder, when used, is present in the amount of 1-20% w/w of the total composition; disintegrant, when used, is present in the amount of 0.1-15% w/w of the total composition; pH adjusting agent, when used, is present in the amount of 0.01-20% w/w of the total composition and lubricant, when used is present in the amount of 0.02-5% w/w of the total composition.

Additionally, pharmaceutical acceptable carrier according to present invention can be any excipients required for formulating composition according to present invention such as glidant, crystal growth inhibitor, surfactant, film forming polymer, plasticizer, buffering agent or complexing agent. Any of such excipients may be used alone or in combination of same/other excipients. Any of the said carriers can be used in the quantity which is suitable for formulating the composition according to present invention.

A diluent is selected from powdered cellulose, microcrystalline cellulose, silicified microcrystalline cellulose, starch, dibasic calcium phosphate, dibasic sodium phosphate, tribasic sodium phosphate; sugars such as dextrose, lactose or sucrose; sugar alcohols such as mannitol, sorbitol, xylitol or erythritol; or mixtures thereof. The diluent may be present in an amount ranging from 10-98% w/w of the total composition.

A binder is selected from starches such as maize starch, corn starch, pregelatinised starch; cellulose derivatives such as cellulose powder, microcrystalline cellulose, hydroxypropyl methylcellulose, ethyl cellulose, methyl cellulose, hydroxypropyl cellulose, polyethylene glycol, hydroxyethyl cellulose; polyvinyl pyrrolidone, gelatin, polymethacrylates, sodium alginate, gums, synthetic resins or mixtures thereof. The binder may be present in an amount ranging from 1-20% w/w of the total composition.

A crystal growth inhibitor is the agent which substantially inhibits the precipitation of compound A. Crystal growth inhibitor may be meglumine, polyoxyethylene-polyoxypropylene block copolymers and the like. The crystal growth inhibitor may be present in an amount ranging from 0.01-20% w/w of the total composition.

A lubricant or glidant is selected from talc, metallic stearate such as magnesium stearate, calcium stearate, zinc stearate; colloidal silicon dioxide, finely divided silicon dioxide, stearic acid, hydrogenated vegetable oil, glyceryl palmitostearate, glyceryl monostearate, glyceryl behenate, sodium stearyl fumarate, magnesium trisilicate; or mixtures thereof. The lubricant or glidant may be present in an amount ranging from 0.02-5% w/w of the total composition.

A surfactant is selected from one or more non-ionic or ionic (i. e., cationic, anionic and Zwitterionic) surfactants suitable for use in pharmaceutical compositions. Suitable surfactants include mono fatty acid esters of polyoxyethylene sorbitan such as those sold under the brand name Tween®; sodium lauryl sulfate, polyoxyethylene castor oil derivatives such as those sold under the brand name Cremophor®, polyethoxylated fatty acids and their derivatives, propylene glycol fatty acid esters, sterol and sterol derivatives; sorbitan fatty acid esters and their derivatives, sugar esters, polyoxyethylene-polyoxypropylene block copolymers such as those sold under the brand name Poloxamer®, soy lecithin, or mixtures thereof. The surfactant may be present in an amount ranging from 0.01-20% w/w of the total composition.

A pH adjusting agent according to present invention is any agent which maintains the pH of the composition, preferably above 3. A pH adjusting agent is either organic or inorganic agent. The non limiting examples of such agent are meglumine, NaOH, KOH, NH3, ammonium hydroxide, carbonates such as sodium carbonate or potassium carbonate and the like. pH adjusting agent also includes buffering agent. The pH adjusting agent may be present in an amount ranging from 0.01-20% w/w of the total composition.

A buffering agent is selected from phosphates such as sodium phosphate, sodium dihydrogen phosphate, sodium dihydrogen phosphate dihydrate, disodium hydrogen phosphate, disodium hydrogen phosphate dodecahydrate, potassium phosphate, potassium dihydrogen phosphate and dipotassium hydrogen phosphate; boric acid and borates such as, sodium borate and potassium borate; citric acid and citrates such as sodium citrate and disodium citrate; acetates such as sodium acetate and potassium acetate; carbonates such as sodium carbonate and sodium hydrogen carbonate and the like. The buffering agent may be present in an amount ranging from 0.01-20% w/w of the total composition.

A disintegrant is sodium starch glycolate, crospovidone, croscarmellose sodium and the like. The disintegrant may be present in an amount ranging from 0.1-15% w/w of the total composition.

A complexing agent is selected from cyclodextrin class of molecules, such as cyclodextrins containing from six to twelve glucose units, especially, alpha-cyclodextrin, beta-cyclodextrin, gamma-cyclodextrin, or their derivatives, such as hydroxypropyl beta cyclodextrins, or mixtures thereof. The complexing agent may be present in an amount ranging from 0.1-20% w/w of the total composition.

Film forming polymers is selected from hydroxpropyl methylcellulose, methylcellulose, ethylcellulose, polyethylene glycol, hydroxypropyl cellulose, povidone, polydextrose, lactose, maltodextrin, acrylic polymer, or mixtures thereof. Film forming polymers may be present in an amount ranging from 0.1-10% w/w of the total composition.

The immediate release composition according to present invention can be uncoated or coated with a suitable coating agent.

An alternative embodiment of the present invention provides a low dose pharmaceutical composition comprising compound A for the treatment of IBD in a mammal, wherein composition provides controlled release of the compound A.

The controlled release composition according to present invention is modified release composition, extended release composition, delayed release composition or composition for site specific delivery of compound A. A controlled release composition is prepared by using suitable amount of at least one pharmaceutical acceptable carrier which provides controlled release of compound A. Preferably, a controlled release composition according to present invention is delayed release composition.

Thus, another embodiment of the present invention provides a low dose pharmaceutical composition for oral administration comprising compound A and at least one pharmaceutically acceptable carrier selected from diluent, binder, disintegrant, pH adjusting agent and lubricant for the treatment of IBD in a mammal, wherein the said composition is substantially insoluble at pH below 5.

Another embodiment of the present invention provides a low dose pharmaceutical composition for oral administration comprising compound A and at least one pharmaceutically acceptable carrier selected from diluent, binder, disintegrant, pH adjusting agent and lubricant for the treatment of IBD in a mammal, wherein the said composition releases at least 50% of the said compound in vivo at pH above 5.

A pharmaceutical composition according to present invention releases at least 50% of the said compound in vivo at pH above 5, preferably pharmaceutical composition according to present invention releases at least 60% of the said compound in vivo at pH above 5, most preferably pharmaceutical composition according to present invention releases at least 70% of the said compound in vivo at pH above 5.

Another embodiment of the present invention provides a low dose pharmaceutical composition for oral administration comprising compound A and at least one pharmaceutically acceptable carrier for the treatment of IBD, wherein the said carrier is suitable for controlled release of the said compound. Preferably, said carrier is suitable for delayed release of the compound A.

A preferred embodiment of the present invention provides a low dose pharmaceutical composition for oral administration comprising compound A and at least one pharmaceutically acceptable carrier suitable for delayed release for the treatment of IBD in a mammal, wherein the said carrier is present in an amount of at least 1% w/w of the total composition. Preferably said carrier is present in amount of at least 2% w/w of the total composition, more preferably said carrier is present in an amount of at least 10% w/w of the total composition, most preferably said carrier is present in an amount of at least 20% w/w of the total composition.

Present invention provides a low dose pharmaceutical composition for delayed release comprising compound A and at least one pharmaceutically acceptable carrier suitable for delayed release for the treatment of IBD in a mammal.

"Pharmaceutically acceptable carrier suitable for controlled release" includes one or more excipients which facilitates controlled release of the compound A. Such excipients include polymeric or non-polymeric compounds, preferably polymeric compounds. Such polymeric compounds may further are water soluble polymers or water insoluble polymers.

"Water-soluble polymer" used in the present composition is polymer which is soluble or swellable in water. Preferably, it dissolves and/or swells in water at room temperatures. Non limiting examples include the cellulose ethers, hydrocolloid (gum), polyvinyl alcohol and polyvinyl pyrrolidone.

The cellulose ethers include carboxymethyl cellulose, methyl cellulose, hydroxyethyl cellulose, hydroxypropyl cellulose, hydroxybutyl cellulose, hydroxyethyl methyl cellulose, hydroxyethylethyl cellulose, hydroxypropylmethyl cellulose, hydroxypropylethyl cellulose, hydroxybutylmethyl cellulose, hydroxybutylethyl cellulose, carboxymethyl cellulose and salts thereof. hydrocolloid (gum) includes guar gum, alginic acid and its pharmaceutically acceptable salts e.g., sodium alginate and xanthan gum "Water insoluble polymer" used in present invention are the polymer which are substantially insoluble in water and include cellulose ethers such as ethylcellulose, butylcellulose, cellulose acetate, cellulose acetate butyrate, ethylene vinyl acetate copolymer, polyvidone acetate, polyvinyl acetate, polyvinyl butyrate, polymethacrylates, including ethylacrylate/methylmethacrylate copolymers, and ammonia methacrylate copolymers, thus including commercially available dispersions such as Kollicoat® MAE30DP, Eudragit® RL30D, Eudragit® NE30D, and Eudragit® RS30D.

A pharmaceutical acceptable carrier suitable for delayed release is any carrier which facilitate the release of the compound A in lower GI tract or which substantially hinders the release of compound A in upper GI tract.

"Pharmaceutically acceptable carrier suitable for delayed release" includes one or more excipients which facilitates delayed release of the compound A. Such excipients include polymeric or non-polymeric compounds, preferably polymeric compounds. Such excipients may be pH dependent or pH independent; preferably pH dependent compounds are used. These excipients include cellulose derivatives, acrylic acid derivatives, maleic acid copolymer, polyvinyl derivatives and the like.

Cellulose derivatives include hydroxypropylmethylcellulose acetate succinate, hydroxypropylmethylcellulose phthalate, hydroxymethylethylcellulose phthalate, cellulose acetate phthalate, cellulose acetate succinate, cellulose acetate maleate, cellulose acetate trimelliate, cellulose benzoate phthalate, cellulose propionate phthalate, methylcellulose phthalate, carboxymethylethylcellulose, ethylhydroxyethylcellulose phthalate and the like.

Acrylic acid derivatives include styrene, acrylic acid copolymer, methyl acrylate, acrylic acid copolymer, methyl acrylate, methacrylic acid copolymer, butyl acrylate styrene acrylic acid copolymer, methacrylic acid, methyl methacrylate copolymer (e.g. Trade-names: Eudragit® L 100 and Eudragit® S), methacrylic acid polymers, ethyl acrylate copolymer (e.g. Trade-name: Eudragit L® 100-55), methyl acrylate, methacrylic acid octyl acrylate copolymer and the like.

Maleic acid copolymer based polymers include vinylacetate maleic acid anhydride copolymer, styrene maleic acid anhydride copolymer, styrene maleic acid monoester copolymer, vinylmethylether maleic acid anhydride copolymer, ethylene maleic acid anhydride copolymer, vinylbutylether maleic acid anhydride copolymer, acrylonitrile, methyl acrylate maleic acid anhydride copolymer, butyl acrylate styrene maleic acid anhydride copolymer and the like.

Polyvinyl derivative based polymers includes polyvinyl alcohol phthalate, polyvinylacetal phthalate, polyvinyl butylate phthalate, polyvinylacetoacetal phthalate and the like.

The pharmaceutical compositions may additionally contain excipients such as colorants selected from known F.D. & C. and D. & C. dyes, titanium dioxide and the like.

A preferred route of administration of pharmaceutical composition according to present invention to the mammals is non parenteral route, most preferably oral route but alternatively intrarectal route can also be used for administration of the composition.

Pharmaceutical composition of the present invention which is free from any pharmaceutically acceptable carrier also forms part of this invention.

The pharmaceutical composition as described herein may be obtained in any suitable form such as tablet, capsule, powder, oral solution, suspension, rectal gel, rectal foam, rectal enema or suppository and the like.

Further embodiment of the present invention provides a process of preparation of a low dose pharmaceutical composition of present invention.

Composition according to present invention can be prepared by any method known in the art such as by mixing the compound A with pharmaceutically acceptable carriers. Alternatively wet granulation or dry granulation techniques may be employed for the preparation of composition according to present invention.

Alternatively, composition of present invention can be prepared as matrix based formulation in which compound A is dispersed within a matrix. Alternatively, compound A containing particles may be coated by suitable pharmaceutically acceptable carriers. Types of particles include granules, pellets, minitablets, microparticles or beads.

Rectal composition may be prepared by a skilled person as known in the art.

Another embodiment of present invention provides method of treating IBD in a mammal by administering pharmaceutical composition of present invention.

Another embodiment of present invention provides use of compound A for the preparation of low dose pharmaceutical composition according to present invention.

Low dose pharmaceutical composition according to present invention can be administered once a day or twice a day to achieve therapeutic effect. Preferably, low dose pharmaceutical composition according to present invention is administered twice a day to achieve therapeutic effect.

The low dose pharmaceutical composition comprising compound A according to present invention may further comprise another agent suitable for treatment of IBD including immune modifier or anti-inflammatory drugs. Alternatively, pharmaceutical composition can be administered along with other agents suitable for treatment of IBD including immune modifier or anti-inflammatory drugs.

The invention according to present invention may be illustrated by the following examples which are not to be construed as limiting the scope of the invention:

Example 1a

| Component | Amount of excipients in mg | | |
|---|---|---|---|
| Compositions | i | ii | iii |
| Compound A | 2.5 | 10 | 40 |
| Mannitol | 20.63 | 22.5 | — |
| Meglumine | 0.63 | 2.50 | 10.00 |
| Microcrystalline cellulose | 55.63 | 42.50 | 10.00 |
| Magnesium stearate | 1.0 | 1.0 | 1.0 |
| Polysorbate | — | — | 2.0 |
| HPMC | 1.0 | 1.0 | 1.0 |
| Sodium Starch Glycolate | 4.63 | 6.50 | 14.0 |
| Hydroxypropyl cellulose | 1.0 | 1.0 | 1.0 |
| Talc | 0.40 | 0.40 | 0.40 |
| Titanium Dioxide | 1.00 | 1.00 | 1.00 |

Microcrystalline cellulose (MCC), mannitol, meglumine and sodium starch glycolate (SSG) were sifted with compound A and dry mixed in Rapid Mixer Granulator (RMG) for 10 minutes followed by granulation with water in RMG. After drying the granules at 60-70° C. in fluid bed dryer (FBD), granules were sized using oscillating granulator followed by blending in conta blender for about 5 minutes. These granules were blended with mixture of MCC, mannitol and SSG for compositions i and ii. Obtained blend was lubricated with Mg stearate using conta blender for about 5 minutes followed by compression in rotatory compression machine to form tablet. Seal coating of HPMC, HPC, talc and titanium dioxide solution in water was applied over prepared tablet. Similar procedure was followed for composition iii.

Example 1b

| Component | Amount of excipients in mg | | |
|---|---|---|---|
| Compositions | i | ii | iii |
| Compound A | 2.5 | 10 | 40 |
| Microcrystalline cellulose | 55.63 | 42.50 | 10.00 |
| Mannitol | 20.63 | 22.50 | 10.00 |
| Meglumine | 0.63 | 2.50 | 10.00 |
| Sodium Starch Glycolate | 4.63 | 6.50 | 14.00 |
| Magnesium stearate | 1.00 | 1.00 | 1.00 |
| HPMC | 1.00 | 1.00 | 1.00 |
| Hydroxy Propyl Cellulose (HPC) | 1.00 | 1.00 | 1.00 |
| Talc | 1.63 | 1.63 | 1.63 |
| Titanium Dioxide | 1.00 | 1.00 | 1.00 |
| Methacrylic acid-Ethylacrylate copolymer (1:1) dispersion 30% | 2.46 | 2.46 | 2.46 |
| Propylene Glycol | 0.74 | 0.74 | 0.74 |

Microcrystalline cellulose (MCC), mannitol, meglumine and sodium starch glycolate (SSG) were sifted with compound A and dry mixed in Rapid Mixer Granulator (RMG) for 10 minutes followed by granulation with water in RMG. After drying the granules at 60-70° C. in fluid bed dryer (FBD), granules were sized using oscillating granulator followed by blending in conta blender for about 5 minutes. These granules were blended with mixture of MCC, mannitol and SSG for compositions i and ii, while with SSG only for composition iii. Obtained blend was lubricated with Mg stearate using conta blender for about 5 minutes followed by compression in rotatory compression machine to form tablet. Seal coating of HPMC, HPC, talc and titanium dioxide solution in water was applied over prepared tablet, which was further coated with enteric coating comprising Methacrylic acid-Ethylacrylate copolymer (1:1) dispersion 30%, propylene glycol and talc. Prepared tablets were stored in HDPE bottle.

In-vitro dissolution profile of the tablets prepared according to Example 1b was tested in 900 mL of Fasted State Simulated Intestinal Fluid having pH 5, i.e 50 mM Sodium acetate/FaSSIF at 37° C. To mimic in-vivo state, dissolution was checked in Simulated Intestinal Fluid having pH 5 with enzymes such as FaSSIF. FaSSIF or Fasted state simulated intestinal fluid is prepared as per USP. In-vitro dissolution at lower pH such as 0.1 N HCl was also assessed. Results are summarized as Table 1:

TABLE 1

| | Composition | | | | | | | | |
|---|---|---|---|---|---|---|---|---|---|
| | Dissolution in 0.1N HCl, 75 RPM, 900 mL, 37° C. | | | Dissolution in 50 mM Sodium acetate/FaSSIF. pH 5.0, 75 RPM, 900 mL, 37° C. at time interval in min Time | | | | | |
| | 1 Hr | 2 Hrs | | 0 | 5 | 10 | 15 | 20 | 30 | 45 |
| Ex 1b (i) | 0 | 0 | Sodium acetate | 0 | 0.0 | 16.1 | 78.8 | 78.8 | 96.6 | 101.2 |
| Ex 1b (i) | 0 | 0 | FaSSIF | 0 | 5.7 | 7.9 | 17.9 | 59.5 | 78.4 | 87.7 |
| Ex 1b (ii) | 0 | 0 | Sodium acetate | 0 | 0.0 | 18.4 | 59.0 | 75.7 | 93.4 | 99.1 |
| Ex 1b (ii) | 0 | 0 | FaSSIF | 0 | 0.0 | 0.0 | 12.6 | 76.2 | 97.9 | 101.6 |
| Ex 1b (iii) | 0 | 0 | Sodium acetate | 0 | 0.0 | 7.7 | 43.9 | 76.1 | 98.6 | 98.0 |
| Ex 1b (iii) | 0 | 0 | FaSSIF | 0 | 0.0 | 0.0 | 0.0 | 14.4 | 62.7 | 97.8 |

Above given results in table 1 show that composition according to present invention is substantially insoluble at acidic pH, specifically at pH below 5 and composition would releases compound A in lower GI tract, i.e. above pH 5.

Example 2

Intrarectal Composition

| Component | Amount of excipients in % |
|---|---|
| Compound A | 2.5-60 mg |
| Poloxamer 407 | 10-30% |
| Polyethylene Glycol | 15-30% |
| Potassium hydrogen Phosphate | 0-5% |

Example 3

Preparation of TNBS Induced Colitis Model

Animal with TNBS (2, 4, 6 trinitrobenzene sulfonic acid) induced colitis is an established model for IBD. Male BALB/c mice were kept for 16 hours fasting and were administered 0.1 ml TNBS solution (containing 1.5 mg of TNBS in 50% ethanol) rectally 4 cm inside the anus with the help of flexible polyethylene catheter under isoflurane anesthesia. Immediately after TNBS administration, mice were held vertically in a head-down position for an additional 45-60 sec to ensure retention and distribution of TNBS solution within the colon of animal. (Fiorucci et al, *Immunity*, 2002; Vol. 17; 769-780)

Example 4

Pharmacokinetic Evaluation of Compound A in TNBS Induced Colitis Model (Intraperitoneal (IP) Administration and Peroral (PO) Administration)

Pharmaceutical composition comprising compound A was administered to mice with TNBS induced colitis (as developed according to example 3) at the dose of 1 mg/kg of compound A twice a day, at 10 ml/kg dosing volume by intraperitoneal route and peroral route. Dosing was initiated a day prior to induction (day −1) of TNBS colitis. Blood samples of treated animals were collected before administration of fifth dose (0 min) and at various time points after fifth dose administration. Blood samples were centrifuged within one hour of collection at 4000 rpm for 10 min at 4° C. and plasma was separated. These plasma samples were analyzed for compound A levels using LC-MS/MS method. Pharmacokinetic parameters of the compound A were calculated by non-compartmental analysis method using Phoenix WinNolin version 6.2. Pharmacokinetic results are summarized in table 2.

TABLE 2

| Parameter | Unit | Per Oral | Intraperitoneal |
|---|---|---|---|
| Cmax | ng/mL | 13.20 | 399.24 |
| $AUC_{0\_12}$ | hr*ng/mL | 63.08 | 255.91 |

Example 5

Effectiveness of Pharmaceutical Composition of Compound A in TNBS Induced Colitis Model (Peroral (PO) Administration)

Pharmaceutical composition comprising compound A was administered orally to mice with TNBS induced colitis (as developed according to example 3) at the dose of 1 mg/kg of compound A twice a day, at 10 ml/kg dosing volume. Dosing was initiated a day prior to induction (day −1) of TNBS colitis. Treatment related attenuation in body weight loss, improved disease activity index (DAI, a composite score ranging from 0 to maximum 12 considering the loss in body weight, fecal consistency and presence or absence of occult blood in feces), healthier colon (macroscopy score) and rate of survival were established in the 6 days treated animals (from day −1 to day 4) to check efficacy of compound A. Body weights were monitored daily, DAI was captured on day 2 and day 4 whereas colonic damage (macroscopy score and histopathological score) was scored based on extent of colonic damage. Histopathological evaluation of colonic damage was performed in formalin fixed colon tissue sections, stained with hematoxylin and eosin, at 10× magnification using Leica® DM2500 microscope, after study completion. Placebo group was given similar composition without compound A. Results are given in. FIG. 1a-1d. (*p<0.05 vs placebo/vehicle {composition without compound A}), FIG. 5 and FIG. 8.

Figure 5:
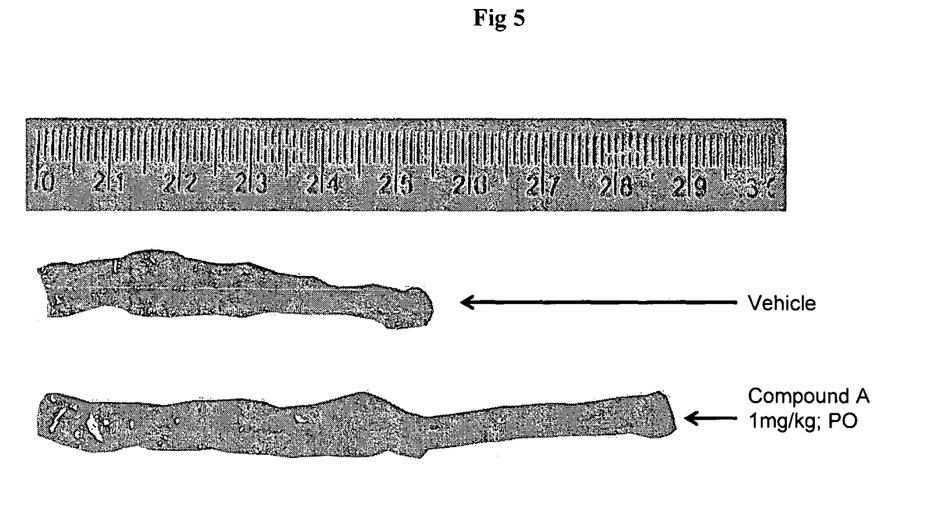
FIG. 5: Colon images of animal model of colitis (TNBS induced colitis in male BALB/c mice) on per-oral administration of pharmaceutical composition comprising compound A at the dose of 1 mg/kg bid or vehicle (Placebo-composition without compound A).
Figure 8:
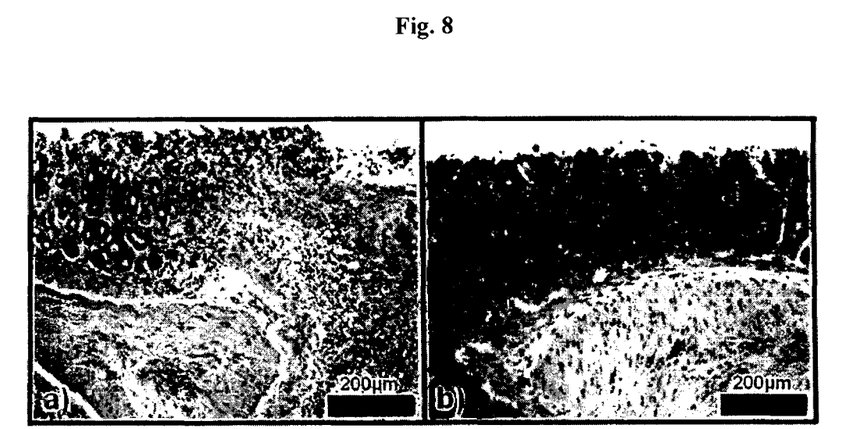
FIG. 8: Crypt architecture and inflammatory cells on per-oral administration of placebo (composition without compound A) (a), 1 mg/kg bid of compound A (b) to animal model of colitis (TNBS induced colitis male BALB/c mice) upon 6 days of treatment

Observation:

Data of table 2 clearly shows that at equal dose of compound A, oral administration was found to provide significantly lower systemic concentration compared to IP administration but still oral dose was found efficacious (FIG. 1a-1d). Results of FIG. 1, FIG. 5 and FIG. 8 show that composition of compound A provided therapeutic benefit by improving the disease activity index, attenuating the extent of colon damage, reducing rate of weight loss and improving survival rate in diseased animals.

Example 6

Comparative Efficacy of Pharmaceutical Composition of Compound A Administered Through Oral Route and Intraperitoneal Route Similar to procedures given above in Example 5, pharmaceutical composition of compound A was administered, twice a day, in mice with TNBS induced colitis through intraperitoneal route and oral route. Treated animals were analyzed for improved disease activity index and healthier colon (macroscopy score). Results are summarized in FIGS. 6a and 6b.

Figure 6A:
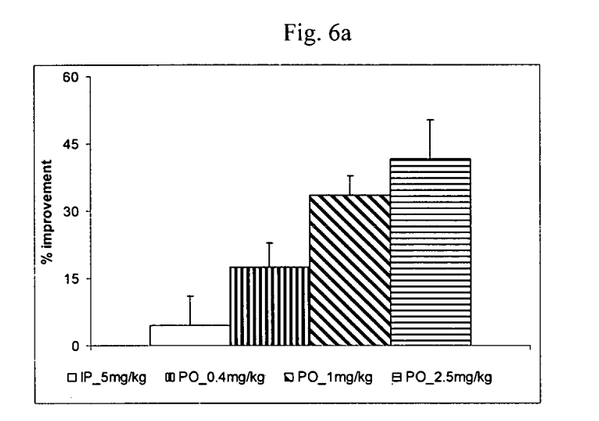
Figure 6B:
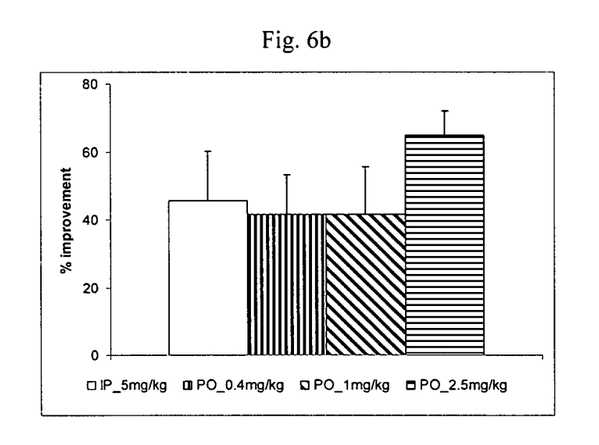

Observation:

Data given in FIGS. 6a and 6b show that oral administration of compound A demonstrated better therapeutic efficacy as compared to IP administration even at lower doses.

Example 7

Effectiveness of Pharmaceutical Composition of Compound A in DSS (Dextran Sodium Sulfate) Induced Colitis Model 5% DSS (MW-36000-50000) dissolved in drinking water was provided to female BALB/c mice for 11 days (Gunther et al, *The Journal of Pharmacology and Experimental*

Figure 1A:
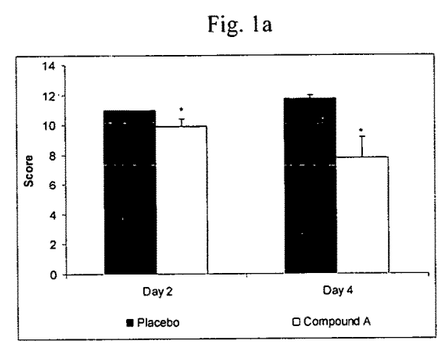
Figure 1B:
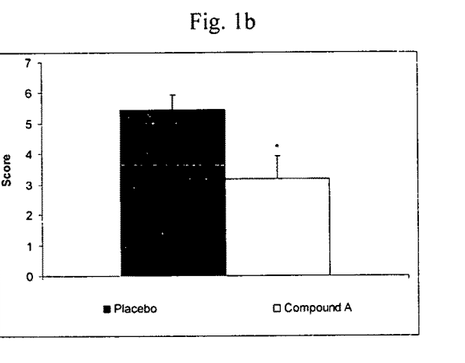
Figure 1C:
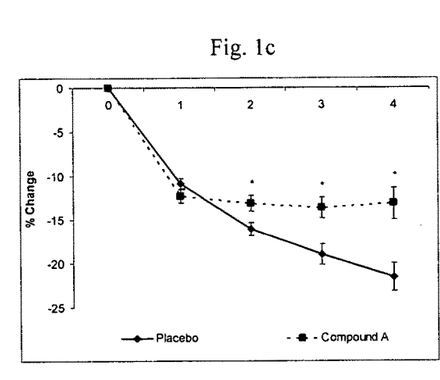
Figure 1D:
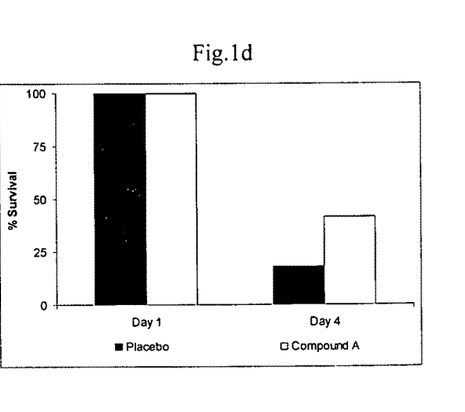
Figure 2A:
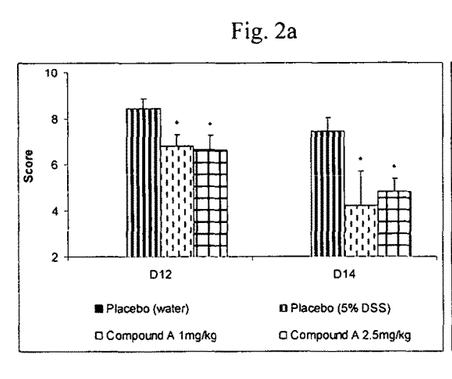
Figure 2B:
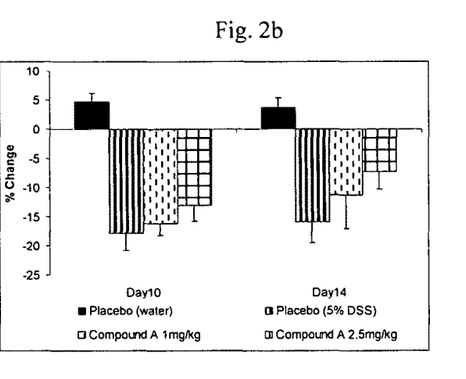
Figure 2C:
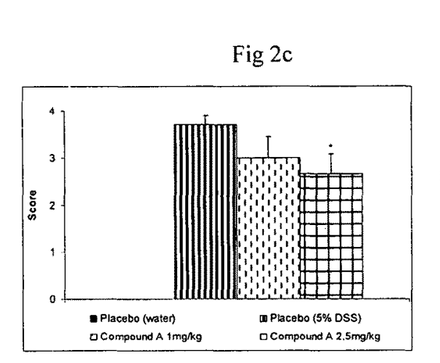

*Therapeutics*, 1999; Vol. 292, No. 1; 22-30) followed by DSS free period till day 14. Pharmaceutical composition comprising compound A was administered to these animals from day 5 to day 14 at the dose of 1 and 2.5 mg/kg of compound A twice a day, at 10 ml/kg dosing volume by oral route (PO). Placebo group was given similar composition without compound A. Placebo (composition without compound A) was also administered to healthy animals, which were given only drinking water and represented as placebo (water). Treatment related attenuation in body weight loss, improved disease activity index (DAI, a composite score ranging from 0 to maximum 12 considering the loss in body weight, fecal consistency and presence or absence of occult blood in feces) and colon histopathology (Score) were established in 10 days treated animals (from day 5 to day 14) to check efficacy of compound A. Body weights were monitored daily, DAI was captured every alternate day whereas histopathological evaluation of colonic damage was performed in formalin fixed colon tissue after study completion, similar to example 5. Results are summarized in FIG. 2a-2c. (*$p<0.05$ vs placebo (5% DSS)) and FIG. 4.

Figure 4:
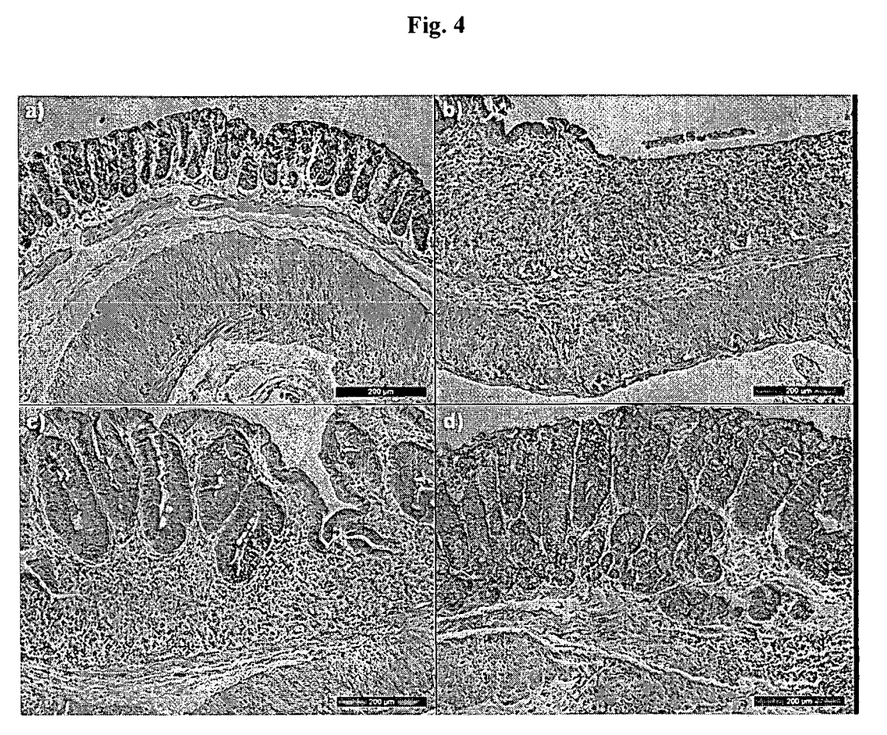
FIG. 4: Crypt architecture and inflammatory cells in colon of healthy animals on peroral administration of placebo (composition without compound A) (a); and on per-oral administration of placebo (composition without compound A) (b), 1 mg/kg bid of compound A composition (c) and 2.5 mg/kg bid of compound A composition (d) to animal model of colitis (DSS induced colitis in female BALB/c mice) upon 10 days of treatment.

Observation:

These results from FIGS. 2 and 4 show that composition of compound A provided therapeutic benefit by reducing the rate of weight loss, improving the disease activity index, attenuating extent of colon damage and preserving tissue architecture in diseased animals.

Example 8

Tissue Distribution of Compound A in DSS Induced Colitis Model

5% DSS (MW-36000-50000) dissolved in drinking water was provided to female BALB/c mice for 7 days. Pharmaceutical composition comprising compound A was administered twice a day to these animals from day 5 orally at the dose of 1 mg/kg of compound A and intraperitoneally at the dose of 0.25 mg/kg of compound A, at 10 ml/kg dosing volume.

Figure 3:
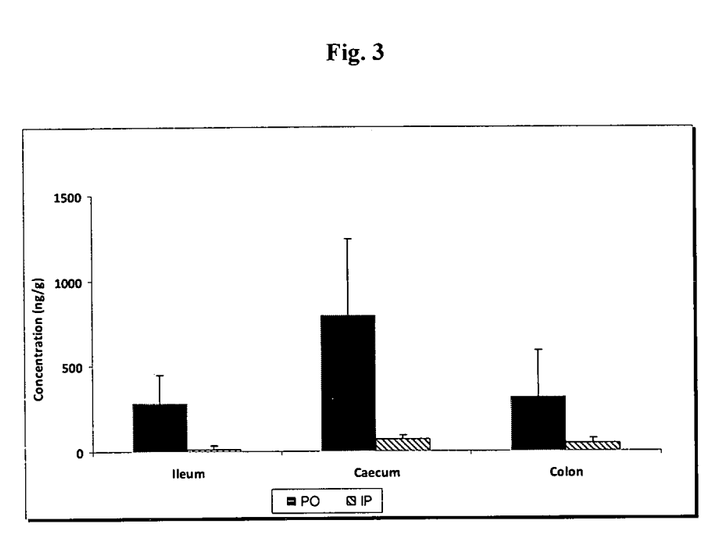
FIG. 3: Tissue distribution of compound A in ileum, caecum and colon after administration of pharmaceutical composition comprising compound A by oral and intraperitoneal route in animal model of colitis (DSS induced colitis in female BALB/c mice).

6 hours after first dose on $7^{th}$ day administration of composition, animals were sacrificed; whole body perfusion through heart using cold phosphate buffered saline was performed followed by collection of tissues of interest, which were further rinsed with PBS buffer for removal of any residual GI content. Plasma and tissue levels of compound A were estimated using LC-MS/MS method. The results are summarized in FIG. 3.

Observation:

Data clearly shows that at four fold differences in dose administered through oral and intraperitoneal route, mean exposure of compound A in tissue of interest via oral administration was found to be 6 to 21-fold higher than achieved with intra-peritoneal administration.

Example 9

Excretion of Compound A in Feces

5% DSS (MW-36000-50000) dissolved in drinking water was provided to female BALB/c mice throughout the study duration of 9 days. Single administration of pharmaceutical composition comprising compound A at the dose of 1 mg/kg of compound A, at 10 ml/kg dosing volume was performed orally on day 5. Feces were collected for 96 hours post administration of the composition. Feces collected was analyzed for compound A levels using LC-MS/MS method. Results are summarized in Table 3.

TABLE 3

| Animals No | Total amount of compound A in feces (µg) | Amount of compound A administered (µg) | % Recovery in feces |
|---|---|---|---|
| 1 | 12.71 | 25.00 | 50.88 |
| 2 | 12.08 | 19.00 | 63.60 |
| 3 | 15.34 | 24.00 | 63.92 |
| 4 | 13.71 | 22.00 | 62.35 |
| 5 | 12.63 | 24.00 | 52.66 |
| Mean % Recovery in feces | | | 58.68 |
| SD | | | 6.37 |

Observation:

Above results from table 3 show that more than 50% of the compound A is recovered from feces, when an oral composition according to present invention was administered to diseased animals.

Example 10

HSP70 Expression in Colon

Effect of oral administration of pharmaceutical composition of compound A on expression of HSP70 was checked in DSS model of colitis.

5% DSS (MW-36000-50000) dissolved in drinking water was provided to female BALB/c mice for 5 days. Single dose of compound A was administered to these animals on day 5. Composition comprising compound A was administered at the dose of 2.5 mg/kg, at 10 ml/kg dosing volume by oral route (PO). Placebo group was given similar composition without compound A. Six hours after administration, animals were sacrificed and colon were processed for whole tissue extract preparation. Proteins were separated on SDS-PAGE followed by immunoblotting, employing HSP70 antibody. The results are presented in FIG. 2d.

Figure 2D:
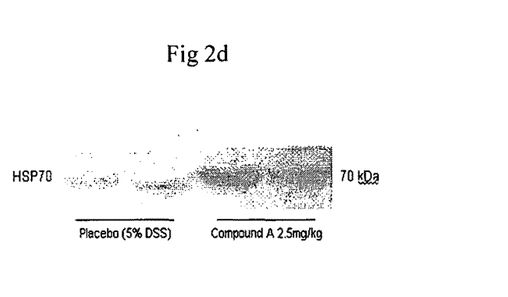

Observation:

It was observed that oral administration of pharmaceutical composition of Compound A resulted in a pronounced induction of HSP70 in colon as compared with the respective placebo (composition without compound A).

Example 11

Inflammatory Marker Expression in Colon

Effect of oral administration of pharmaceutical composition of compound A on expression of interleukin (IL)-10, TNF-α, and interferon (INF)-γ mRNA was assessed in DSS model of colitis.

Pharmaceutical composition comprising compound A was administered 2.5 mg/kg twice a day from day 5 to day 14 to DSS induced colitis mice (as developed according to example 7) by oral route (PO). Animals were sacrificed on day 14 and colon were processed for whole tissue extract preparation. Expression of interleukin (IL)-10, TNF-α, and interferon (INF)-γ mRNA along with expression of 18S rRNA was monitored employing gene specific primer and probes (Applied Biosystems, Foster City, Calif., USA) by quantitative real-time polymerase chain reaction on ABI 7900 HT (Applied Biosystems, Foster City, Calif., USA). mRNA expression was normalized relative to the expression of 18S rRNA. Placebo group was given similar composition without compound A. The results, as given in FIG. 7, were expressed as fold induction relative to placebo (composition without compound A).

Figure 7:
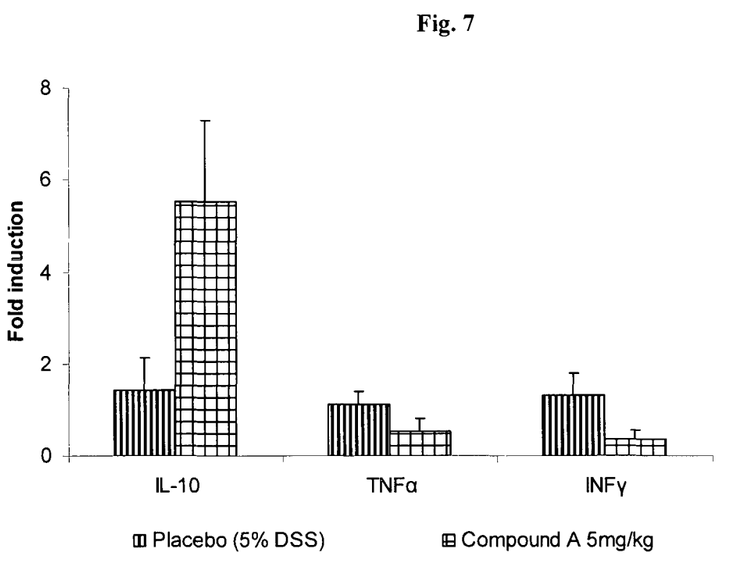
FIG. 7: mRNA expression of IL-10, TNF-$\alpha$, and INF-$\gamma$ in colon tissue of animal model of colitis (DSS induced colitis in female BALB/c mice) on 2.5 mg/kg bid (5 mg/kg/day) per-oral administration of pharmaceutical composition comprising compound A or placebo (composition without compound A).

Observation:

It was observed that oral administration of pharmaceutical composition of Compound A resulted in reduction of expression of pro-inflammatory cytokines, TNFα and INFγ and elevation in the expression of the anti-inflammatory cytokine IL-10.

We claim:

1. A method of treating inflammatory bowel disease in a human, the method comprising administering to the human a pharmaceutical composition comprising a therapeutically effective amount of [(2-hydroxy-4-oxo-6,7,8,9-tetrahydro-4H,5H-10-thia-1,4a-diaza-benzo[a]azulene-3-carbonyl)-amino]-acetic acid ("Compound A") or its pharmaceutically acceptable salt,
wherein the therapeutically effective amount of Compound A ranges from 2.5 mg to 60 mg.

2. The method according to claim 1 wherein Compound A is present in the pharmaceutical composition in an amount that ranges from 4.5 mg to 50 mg.

3. The method according to claim 1 wherein Compound A is present in the pharmaceutical composition in an amount that ranges from 4.5 mg to 40 mg.

4. The method according to claim 1, wherein the pharmaceutical composition further comprises at least one pharmaceutically acceptable carrier selected from the group consisting of a diluent, binder, disintegrant, pH adjusting agent, and lubricant.

5. The method according to claim 2, wherein the pharmaceutical composition further comprises at least one pharmaceutically acceptable carrier selected from the group consisting of a diluent, binder, disintegrant, pH adjusting agent, and lubricant.

6. The method according to claim 3, wherein the pharmaceutical composition further comprises at least one pharmaceutically acceptable carrier selected from the group consisting of a diluent, binder, disintegrant, pH adjusting agent and lubricant.

7. The method of claim 1, wherein the pharmaceutical composition is for non-parenteral administration.

8. The method of claim 7, wherein the non-parenteral administration is oral.

9. The method of claim 2, wherein the pharmaceutical composition is for non-parenteral administration.

10. The method of claim 9, wherein the non-parenteral administration is oral.

11. The method of claim 3, wherein the pharmaceutical composition is for non-parenteral administration.

12. The method of claim 11, wherein the non-parenteral administration is oral.

* * * * *